(12) United States Patent
Graus et al.

(10) Patent No.: US 6,492,429 B1
(45) Date of Patent: Dec. 10, 2002

(54) COMPOSITION FOR THE TREATMENT OF OSTEOARTHRITIS

(75) Inventors: Ivo Maria Franciscus Graus, Wg Ede (NL); Hobbe Friso Smit, As Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/662,123

(22) Filed: Sep. 14, 2000

Related U.S. Application Data

(63) Continuation of application No. 09/613,562, filed on Jul. 10, 2000.

(51) Int. Cl.[7] .......................... A01N 35/00; A01N 65/00
(52) U.S. Cl. ....................................... 514/688; 424/725
(58) Field of Search .......................... 424/195.1, 196.1, 424/523, 547; 514/54, 62, 365, 783, 688; 260/468, 294.8, 470

(56) References Cited

U.S. PATENT DOCUMENTS

| | | | |
|---|---|---|---|
| 3,950,387 A | * | 4/1976 | Joullie et al. ............... 260/468 |
| 4,315,028 A | * | 2/1982 | Scheinberg ................. 424/290 |
| 5,120,538 A | * | 6/1992 | Oei ........................ 424/195.1 |
| 5,401,777 A | | 3/1995 | Ammon et al. |
| 5,494,668 A | | 2/1996 | Patwardhan |
| 5,629,351 A | | 5/1997 | Taneja et al. |
| 5,872,124 A | * | 2/1999 | Koprowski et al. ......... 514/261 |
| 5,888,514 A | * | 3/1999 | Weisman ................. 424/195.1 |

FOREIGN PATENT DOCUMENTS

| | | |
|---|---|---|
| WO | 95 22323 | 8/1995 |
| WO | 97 07796 | 3/1997 |

OTHER PUBLICATIONS

Balch et al. Prescription for Nutritional Healing; Avery Publishing 2nd Ed. pp. 138–144, Oct. 1997.*

Lafeber et al., "Apocynin; a plant–derived, cartilage–saving drug, might be useful in the treatment of rheumatoid arthritis ", *Rheumatology*, (1999), pp. 1088–1093, vol. 38, British Society for Rheumatology.

* cited by examiner

*Primary Examiner*—Christopher R. Tate
*Assistant Examiner*—Patricia A Patten
(74) *Attorney, Agent, or Firm*—Browdy and Neimark, P.L.L.C.

(57) ABSTRACT

Osteoarthritis is treated by a composition containing both apocynin and an inhibitor of inducible nitric oxide synthase such as curcumin. Further components such as boswellic acids, glucosamine, acetylcysteine and boron further enhance the beneficial effect of apocynin and curcumin.

8 Claims, No Drawings

COMPOSITION FOR THE TREATMENT OF OSTEOARTHRITIS

CROSS REFERENCE TO RELATED APPLICATION

The present application is a continuing application from copending application Ser. No. 09/613,562, filed Jul. 10, 2000.

FIELD OF THE INVENTION

The invention is concerned with compositions for the treatment of osteoarthritis and related diseases and with methods for treating osteoarthritis.

BACKGROUND OF THE INVENTION

Osteoarthritis (OA) is a degenerative joint disease, which develops by wear and tear of the joints during aging. OA mostly affects the weight-bearing joints such as spine, knees and hips, but thumb and finger joints may also be affected. Repetitive mechanical injury of the cartilage eventually results in loss of cartilage and damage to joint surfaces and adjacent bone. As a result of the tissue destruction, inflammatory cells invade the joint and the synovial membrane which is manifested by pain, swelling and stiffness of the affected joints. The repetitive mechanical injury leads to pathological changes that result in loss of proteoglycans and collagen from the cartilage matrix, which in turn leads to surface erosion and decreased loading capacity, In OA, chondro-cytes show a reduced potential to synthesize matrix constituents (proteoglycans and collagen fibers) and the expression of proteolytic enzymes (called matrix metalloproteases, MNMP's) contributes to cartilage destruction and release of proteoglycan fragments in the synovial fluid. The inflammatory responses to the mechanical insults further contribute to cartilage destruction. The inflammatory mediator interleukin I (IL-1) is considered as the principal mediator of cartilage destruction. It induces a number of changes in chondrocytes, including the concurrent generation of significant amounts of NO (nitrogen oxide) and superoxide radicals by inducible NO synthase (iNOS) and NADPH oxidase, respectively. NO reacts with superoxide to form peroxynitrite, which is largely responsible for the decrease in proteoglycan synthesis induced by IL-1. The role of superoxide was further demonstrated by the ability of superoxide dismutase to reverse the decrease in proteoglycan synthesis. The prevention of peroxynitrite formation via selective inhibition of iNOS and thus NO formation in vivo resulted in a marked decrease of MMP's. In addition, intra-articular treatment of OA patients with superoxide dismutase reduces symptoms of OA for prolonged periods. These studies demonstrate that induction of catabolic enzymes (MMP's) and cartilage destruction is mediated via the formation of NO and $O_2^-$ radicals by chondrocytes or inflammatory cells. While the primary cause of OA is mechanical damage, rheumatoid arthritis (RA) is mainly the result of an autoimmune response that leads to chronic inflammation in the joint. Contrary to OA, typical manifestations of RA are an increase of parameters that are associated with inflammation, such as haematocrite and white blood cell count and pannus formation or hyperplasia of the joint capsule that leads to deformed joints. This in turn leads to morning stiffness. Although the (primary) aetiology of RA and OA are different, the pathological processes at a later stage result in some manifestations that are similar such as joint pain, cartilage degradation and general joint disability.

Lafeber et al. (*Rheumatology*, 1999 (38) 1088–1093) describe in vitro studies on the utility of apocynin (4-hydroxy-3-methoxy-acetophenone, acetovanillone) for the treatment of rheumatoid arthritis.

WO 95/22323 describes the use of analogues of apocynin, in particular the 4-hydroxyethoxy analogue, for controlling free radical generation by inflammatory cells in e.g. inflammatory bowel disease, rheumatoid arthritis and several other inflammatory conditions.

U.S. Pat. No. 5,629,351 discloses a fraction of boswellic acids isolated form *Boswellia serrata*, including a hitherto unknown 2-hydroxyboswellic acid, having anti-inflammatory, anti-arthritic and anti-ulcerogenic activities. WO 97/07796 claims the use of boswellic acid for the treatment of diseases, such as lung emphysema, cystic fibrosis, rheumatoid arthritis etc, which are induced by leucocytic elastase or plasmin activity.

U.S. Pat. No. 5,401,777 relates to the use of curcumin for treating conditions associated with formation of leucotrienes from arachidonic acid, such as inflammatory bowel diseases, chronic hepatitis, bronchial asthma and psoriasis.

U.S. Pat. No. 5,494,668 describes a product to be used for the treatment of OA and other musculoskeletal diseases, containing combined extracts from *Withania somnifera* (Ashwaganda) roots, *Boswellia serrata* (Sallai guggul) gum exudate (boswellic acids), *Curcuma longa* (turmeric) rhizomes (curcumin) and *Zingiber officinale* (ginger).

SUMMARY OF THE INVENTION

It was found that osteoarthritis can be effectively treated by administration of a suitable amount of apocynin or its functional and structural analogues, preferably in the form of an extract from a Picrorhiza plant, and preferably together with further components enhancing the beneficial effect of the apocynin. Thus, the invention in a first aspect provides compositions for the treatment of osteoarthritis, containing an effective amount of apocynin or its analogues.

In a second aspect, the invention provides methods for treating osteoarthritis comprising administering to a person in need of said treatment an effective amount of apocynin or its analogues. In a third aspect, the invention provides compositions comprising apocynin or analogues and methods for the treatment of arthritis in general as caused by wear-and-tear processes, due to labour, ageing or obesity, for the treatment of developed arthritis and for the-treatment of the first symptoms of joint disorders in patients not having a familial history of rheumatism.

In a fourth aspect the invention provides compositions that are characterized by the simultaneous presence of apocynin or analogues and other components, in particular an inhibitor of inducible nitric oxide synthase and methods for treatment of arthritis in general caused by wear-and-tear, autoimmune responses in the joints, goute, or other causes of cartilage degradation.

DETAILED DESCRIPTION OF THE INVENTION

According to the invention apocynin is a highly useful component for treating osteoarthritis and related conditions. In particular, apocynin was found to be effective in retarding progression of osteoarthritis. It was found furthermore, that the inflammatory processes in arthritis can be controlled and the accompanying symptoms of stiffness and pain can be alleviated by combined administration of an inhibitor of NADPH oxidase, such as apocynin, and an inhibitor of inducible nitric oxide synthase (iNOS), such as curcumin.

Consequently, the composition of the invention contains at least 50 µg, preferably at least 100 µg, up to 1000 mg of apocynin on the basis of daily intake. The preferred daily intake is between 1 and 100 mg. Apocynin (acetovanillone) is a known compound (4-hydroxy-3-methoxyacetophenone); most preferred is a dosage of at least 15 mg/day. According to the invention, analogues of apocynin may be used instead of or in addition to apocynin. Such analogues are in particular those in which the 4-hydroxyl group is etherified, especially with a hydroxylated alkyl group, such as 2-hydroxyethyl, 2,3-dihydroxypropyl or a sugar moiety. The latter analogue in which the sugar moiety is β-D-glucose, is commonly known as androsin. This is the usual form in which apocynin is present in fresh plants.

Preferably apocynin and/or its analogues are present in an extract obtained from apocynin- or androsin-containing plant or plant parts, such as Picrorhiza species, for example *P. kurrooa* and *P. scrophulariiflora*; the latter is also known as *Neopicrorhiza scrophulariiflora*. Cucurbitacins are known to be present in both Picrorhiza species (Stuppner et al., 1991, Wang et al., 1993). As some cucurbitacins are reported to induce immune responses and might potentially lead to adverse health effects, a prepartion is preferably chosen in which cucurbitacins are largely absent, i.e. in which the cucurbitacin level is lower than 40%, preferably lower than 20%, especially lower than 10% of the level of apocynin or its analogue. The total daily intake of cucurbitacins should preferably be below 10 mg, more preferably below 4 mg.

The Picrorhiza extract can be obtained by extracting the rhizomes (roots) of Picrorhiza species or by subjecting an extract to column chromatography. Alternatively, extracts with high amounts of phenolic compounds can be obtained by pretreating the plant material with mineral acid to convert glycosides to their respective aglycones (e.g. androsin to apocynin). If desired, the material may then be defatted shortly to remove wax and other highly lipophilic matter. The material is extracted, for example with ethyl acetate and/or ethanol. The organic solvent is removed and an aqueous solution is obtained. The pH of the extract is increased to 10, e.g. with sodium hydroxide, to deprotonate phenolic compounds and to retain them in the aqueous phase. The aqueous solution is then washed e.g. with diethyl ether to remove cucurbitacins. The aqueous phase is then reacidified to neutralise phenolic compounds and again extracted with e.g. diethyl ether. The organic phase is collected and the solvent removed.

Apocynin may also be obtained from other sources, e.g. from the rhizome of Canadian hemp (*Apocymum cannabinum*) or other Apocynum species (e.g. *A. androsaemifolium*) or from the rhizomes of Iris species, provided that the extracts do not contain substantial amounts of cardiac glycosides.

Although the inventors do not wish to be bound by a specific theory, it is believed that the inhibitory effect of apocynin on NADPH oxidase restores the human system's potential to prevent cartilage destruction that is associated with osteoarthritis.

This effect of apocynin was found to be enhanced by compounds that are capable of inhibiting inducible NO synthase (iNOS) and thus to reduce the formation of peroxynitrite. These combined effects are believed to be important in an effective control of the inflammation and its consequences in OA and OA-related diseases. Thus, the composition according to invention preferably also contains a component that inhibits iNOS. Phenolic compounds, in particular those which contain at least a p-hydroxycinnamoyl group (HO—$C_6H_4$—CH=CH—CO—, p-coumaroyl), preferably a 3,4-di-hydroxycinnamoyl (caffeoyl) or 4-hydroxy-3-methoxycinnamoyl (feruloyl) group, and/or a dihydroxyphenyl group, preferably a dihydroxybenzopyran group, were found to be useful in this respect. Examples of suitable phenolic compounds include curcuminoids, resveratrol, quercetin and other hydroxyflavones, catechins such as epicatechin, catechin, gallocatechin, afzelechin, epigallocatechin gallate, epicatechin gallate, compounds having activated phenolic groups as do occur in ginkgo biloba extracts, luteolin but also procyanidins, caffeic acid, chlorogenic acid, ferulic acid, carnosic acid and rosmarinic acid and their natural derivatives as occur in herb extracts appeared to be useful in this respect. The amount of iNOS inhibitor is preferably between 200 µg and 2000 mg per day; most preferably between and 20 and 500 mg/day.

Especially suitable are curcuminoids. These compounds are obtainable from plant parts, especially rhizomes of Zingiberaceae. A common prominent member of this family is *Curduma longa*. Curcumin (1,7-bis(4-hydroxy-3-methoxyphenyl)hepta-1,6-dien-3,5-dione) is the most prominent example of these active compounds. The recovery of curcumin from Curcuma rhizomes is well-known in the art. It is especially preferred to use preparations that comprise more than 85% curcumin, in particular more than 92% curcumin in order to avoid undesired side effects.

Said combination of apocynin and iNOS inhibitors is advantageously combined with other components that can further enhance the effects such as:

boswellic acids: these can be obtained by extracting Boswellia (Sabinsa) in particular *Boswellia serrata* by applying methods known in the art. It is preferred to use an acid fraction that comprises at least 15% and more preferably more than 23% boswellic acids; between 10 and 1000 mg preferably 80–400 mg should be administered per day; the boswellic acids are usually assayed as 65% of the boswellia extract, based on acid titration; this level, however, corresponds to a true boswellic acid level of about 25%;

glucosamine can be administered as sulfate or chloride salt or other food-grade form in an amount between 750–2500 mg preferably between 1 and 2 g;

chondroitin can be administered in an amount of 0.6–2.4 g, e.g. as sulfate but preferably in a form that is better available, between 10 and 500 mg gingerols, preferably isolated from ginger oil, extract from (*Urtica dioica* especially from the leaves, N-acetyl cysteine in an amount per daily dose of 50 mg and 1 g, preferably 0.1–0.8 g, optionally as equivalent cysteine or thioproline;

boron 1–20 mg preferably 2–10 mg, e.g. as inorganic salt, manganese 0.5–20 mg, preferably 1–10 mg and as inorganic salt such as MnO;

vitamins, minerals and trace elements such as vitamin B5, B6, C, D, E, folic acid, zinc and selenium.

The products according to the invention can be supplements such as tablets, pills, concentrates, powders, bars or cereals sauces, emulsions, liquids, or other dietetic preparations that can comprise the active components. The preparations are meant to be used for oral administration.

EXAMPLE 1

The following components were mixed and tabletted to the following amounts per tablet:

| Component | amount | unit |
|---|---|---|
| active ingredients | | |
| Glucosamine sulfate (potassium) | 331,6 | mg |
| Boswellia serrata extract (65% boswellic acids) | 102,6 | mg |
| Picrorhiza kurrooa extract (10% apocynin) | 33,3 | mg |
| Turmeric root extract (95% curcumin) | 8,8 | mg |
| N-Acetyl cysteine 99% | 84,2 | mg |
| Boron citrate 5% | 10 | mg |
| D-α-Tocopherol succinate 1162 IU/g (vit. E) | 1,5 | mg |
| Ascorbic acid 95% (vit. C) | 3,6 | mg |
| Pyridoxin.HCl, powder (vit. B6) | 130 | µg |
| Vitamin D-3 500 IU/mg | 50 | µg |
| Calcium D-pantothenate, USP | 660 | µg |
| Folic acid, USP, FCC | 280 | µg |
| Zinc oxide, USP | 1,0 | mg |
| Selenium yeast 0.2% Se OB | 2,2 | mg |
| Manganese sulfate monohydrate | 1,1 | mg |
| excipients | | |
| povidone | 28 | mg |
| microcrystalline cellulose granulate | 200 | mg |
| dicalcium phosphate dihydrate | 194 | mg |
| croscarmellose Na, NF | 55 | mg |
| silicon dioxide | 6 | mg |
| stearic acid vegetable source | 27 | mg |
| vegetable stearate | 9 | mg |
| white film coat sol'n | 185 | mg |
| isopropyl alcohol USP | 60 | mg |
| aqueos film coat base clear | 79 | mg |
| corn starch, bleached | 18 | mg |
| pharm. glazes DA45A, 4LB | 16 | mg |

Six tablets were administered per day for effective treatment of arthritic conditions.

EXAMPLE 2

The following active components were mixed into daily dosages:

| Component | amount | unit |
|---|---|---|
| Glucosamine sulfate (potassium) | 1500 | mg |
| Chondroitin sulfate | 1200 | mg |
| Picrorhiza kurrooa extract (10% apocynin) | 20 | mg |
| Rosemary extract | 250 | mg |
| Resveratrol (grape skin extract) | 500 | µg |
| Urtica dioica extract | 750 | mg |

EXAMPLE 3

The following active components were mixed into daily dosages:

| Component | amount | unit |
|---|---|---|
| Glucosamine sulfate (potassium) | 1500 | mg |
| Chondroitin sulfate | 1200 | mg |
| Picrorhiza kurrooa extract (10% apocynin) | 20 | mg |
| Ginger oil | 500 | mg |
| Ginkgo biloba extract | 400 | mg |
| Pine bark extract | 400 | mg |
| Green tea extract | 400 | mg |

We claim:

1. A composition for treating osteoarthritis comprising an effective amount of apocynin or an analogue thereof effective for the treatment of osteoarthritis, from 200 µg to 2000 mg of an inhibitor of inducible nitric oxide synthase per daily dose, and 10 mg to 1 g of at least one boswellic acid per daily dose.

2. The composition according to claim 1 wherein the effective amount of apocynin or its analogues is between 1 mg and 100 mg per daily dose.

3. The composition according to claim 2 wherein the weight ratio of apocynin or its analogue to curcubitacin in the extract is at least 5.

4. The composition according to claim 1 wherein the apocynin is part of an extract of a plant species of Picorhiza or Neopicrohiza.

5. The composition according to claim 1 wherein the inhibitor of inducible nitric oxide synthase comprises a phenolic compound containing at least one member selected from the group consisting of 4-hydroxycinnamoyl groups and dihydroxyphenyl groups.

6. The composition according to claim 5 wherein the inhibitor of inducible nitric oxide synthase comprises curcumin or an analogue thereof.

7. The composition according to claim 6 wherein said curcumin is part of an extract of a plant species of Curcuma.

8. The composition according to claim 1 wherein said boswellic acids are part of an extract of a plant species of Boswellia.

* * * * *